United States Patent [19]

Neeley et al.

[11] 4,260,257
[45] Apr. 7, 1981

[54] FLOW CELL

[76] Inventors: William E. Neeley, 6152 Cardeno Dr., La Jolla, Calif. 92037; Hugh Y. Yee, 4201 Frostwood Ct., Troy, Mich. 48098

[21] Appl. No.: 42,789

[22] Filed: May 29, 1979

[51] Int. Cl.³ .............................................. G01N 21/05
[52] U.S. Cl. ..................................... 356/246; 356/410
[58] Field of Search ............... 356/246, 410, 411, 440; 250/576

[56] References Cited

U.S. PATENT DOCUMENTS

| | | | |
|---|---|---|---|
| 3,583,817 | 6/1971 | Rachlis et al. | 356/410 |
| 3,954,341 | 5/1976 | Uffenheimer | 356/410 |

FOREIGN PATENT DOCUMENTS 2001752  2/1979  United Kingdom ..................... 356/246

Primary Examiner—Vincent P. McGraw
Attorney, Agent, or Firm—Charles C. Logan, II

[57] ABSTRACT

A flow cell for location intermediate a light source and a photosensitive device for light measurement of a fluid therein in a light path. The flow cell has an elongated tubular body member, a debubbler unit, and a tubular fluid outlet tower. The body member has an open-ended bore therethrough constituting a sight passageway. A pair of light transmitting quartz rods are positioned in the respective open ends of the bore to close them. One end of the debubbler unit functions as a fluid inlet conduit and a tubular neck portion extends from the bottom of the debubbler unit and is transversely connected to the open-ended bore of the body member intermediate its ends. A tubular fluid outlet tower has its bottom end transversely connected to the open-ended bore of the body member intermediate its ends. The bottom ends of the debubbler unit and the fluid outlet tower connect to the bore of the body member adjacent the respective internal ends of the light transmitting rods to define the path for fluid flowing through the sight passageway. The internal end surface of the light transmitting rods are flat in the central portion and form a curved surface adjacent their perimeter with the interior surface of the bore of the body member.

6 Claims, 5 Drawing Figures

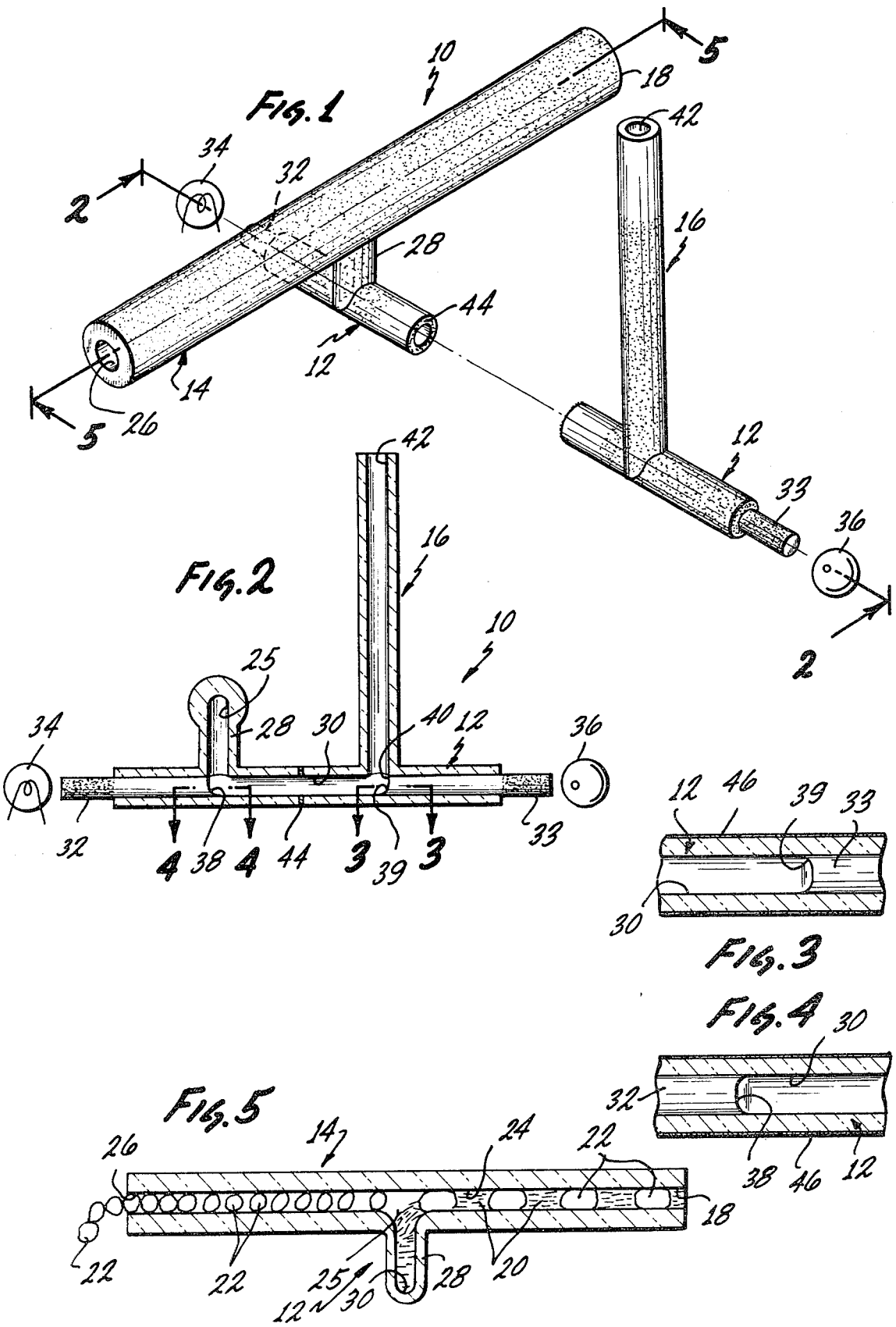

FLOW CELL

BACKGROUND OF THE INVENTION

This invention relates to automatic analysis apparatus and more particularly, to such apparatus which includes a colorimeter flow cell device for the quantitative colorimetric analysis of a fluid stream in respect to an ingredient thereof. Such apparatus is shown and described in U.S. Pat. No. 3,804,593. The apparatus may be used for the chemical analysis of a stream of a series of individual clinical or industrial samples, or for monitoring a continuous sample-liquid stream, for example but without limitation, in an industrial plant to monitor a manufacturing process, a waste stream, etc.

Heretofore, flow cells of tubular glass, with sight passageways, having at their respective ends bent or curved liquid inlet and outlet portions, have been constructed by glass-blowing or lamp-working techniques. Such a flow cell is disclosed in U.S. Pat. No. 3,241,432.

A flow cell formed in this manner may exhibit good laminar flow characteristics. However the bent or curved glass at the respective ends of the cell passageway through which light is directed often fails to exhibit optimum optical qualities. For example, some light from the source may be absorbed in the end walls or refracted therefrom instead of passing substantially axially along the cell passageway. In addition, optical problems have resulted in part because of lack of uniformity in the curved end walls of such a flow cell, and lack of uniformity of one cell with reference to another.

Attempts have been made to improve the optical qualities of a flow cell by the construction of flat end windows for the sight passageway, which windows have been constructed and assembled so as to have their inner and outer surfaces parallel and lying in planes normal to the axis of the tubular body forming the sight passageway. Such a flow cell is disclosed in U.S. Pat. No. 3,345,910. While this construction lessened the afore mentioned refraction problem which resulted from the curved or bent liquid inlet and outer portions of the cell type first described above, and resulted in better uniformity in the end walls of such a flow cell, it did not solve the problem of effectively limiting loss of light from within the end windows such as by transmission directly to the material of the cell body at the interfaces of the latter with the windows. The end windows of this flow cell are glass as is the body of the flow cell.

It has been found in the use of such windowed flow cells that stagnant regions tend to form in the sight passageway. Particulate foreign matter and very fine bubbles, considerably smaller than the passageway, tend to accumulate in these regions. It has been noted that this stagnation occurs particularly in the ends of the sight passageways, next to the windows. More specifically, it has been observed that dirt and small bubbles tend to collect at the bottoms of the windows. It is believed by some that this accumulation is at its greatest at the window near the liquid outlet from the sight passageway. Liquid in such analysis systems is normally pulsed, and when such pulsations occur in a windowed flow cell, such as described above, dirt and bubbles tend to spurt upwardly from the bottom of the sight passageway in a direction across the windows. This particulate foreign matter and small bubbles tend to obscure such a sight passageway, particularly the windows thereof. This results in what is known as optical noise in the signals transmitted from the flow cell to the light detector, which in turn effects a nonlinear affect in the operation of an analysis system such as that disclosed in U.S. Pat. No. 3,804,593.

Prior art flow cells such as illustrated in U.S. Pat. No. 3,583,817, have been designed to overcome the problems that have occurred previously when the inner surfaces of the end windows made a perpendicular angle with respect to the axis of the passageway of the flow cell.

SUMMARY OF THE INVENTION

Applicants novel flow cell is constructed by assembling together tubular components which are then heated to form an integral flow cell member. The novel flow cell has a tubular body member, a debubbler unit, and a tubular fluid outlet tower. The tubular body member has an open ended bore therethrough constituting a sight passageway to lie along a portion of the length of the light path of a colorimeter. The body member is made from quartz material. A pair of fluid seals in the respective open ends of the bore close these ends and each of these seals is a light transmitting rod made from quartz material.

One end of the debubbler unit functions as the fluid inlet. The debubbler unit is oriented transversely to the open-ended bore intermediate its ends and it has a tubular neck portion extending downwardly from its bottom that opens to the bore adjacent the internal end of one of the afore mentioned light transmitting rods. The debubbler unit is also made of quartz material. The tubular fluid outlet tower has its bottom end opening into the bore adjacent the internal end of the other light transmitting rod. The tubular fluid outlet tower is also made of quartz material. The internal end surfaces of the light transmitting rods have a central portion that is flat and substantially perpendicular to the axis of the bore of said tubular member to provide optimal transmission of light and a curved surface adjacent their perimeter that blends with the interior surface of the bore where the respective surfaces meet much in the manner of the meniscus curved surface that is formed by a liquid in a vessel due to surface tension of the liquid with the side walls of the vessel. This curved surface is produced when the flow cell is heated to a predetermined temperature causing the quartz material of the light transmitting rods to fuse to the quartz material of the tubular body member.

The tubular body member also has a transversely oriented opaque barrier within its cross-section that prevents light from passing longitudinally from one end to the other opposite end through the wall structure of the body member. This opaque barrier is formed in the flow cell by breaking the tubular body member at a predetermined location during its manufacturing operation and applying an opaque coating to the surfaces previously broken apart.

The two pieces of tubular body member are then sealed back together again. The outside surface of the tubular body member is also covered by an opaque coating.

It is object of the invention to provide a novel flow cell having a debubbler unit formed integrally therewith.

It is also an object of the invention to provide a novel flow cell having the tubular body member and the light transmitting rods both made from quartz material.

It is also an object of the invention to provide a novel flow cell having a fluid flow path through the bore of the tubular body member that is free of any 90 degree corners.

It is a further object of the invention to provide a novel flow cell that is more efficient in that it will require less use of costly reagents that are added to fluid specimens processed through the flow cell.

It is an additional object of the invention to provide a novel flow cell that has structure to prevent stray light from streaming longitudinally the length of the flow cell along the walls of the tubular body member to cause inaccuracy in the colorimeter output readings, thus resulting in non-linear results.

DESCRIPTION OF THE DRAWINGS

FIG. 1 is a perspective view illustrating schmatically how the novel flow cell is used;

FIG. 2 is a cross sectional elevation view of the novel flow cell;

FIG. 3 is a cross section taken along lines 3—3 of FIG. 2;

FIG. 4 is a cross section taken along lines 4—4 of FIG. 2; and

FIG. 5 is a cross section taken along lines 5—5 of FIG. 1.

DESCRIPTION OF THE PREFERRED EMBODIMENT

The novel flow cell will now be described by referring to FIGS. 1-5 of the drawings. The flow cell is generally designated numeral 10. It has a tubular body member 12, a debubbler unit 14 and a tubular fluid outlet tower 16.

The debubbler unit 14 has a fluid inlet port 18 that is connected to the manifold of an automatic analysis apparatus (not Shown). In the operation of the analysis apparatus, fluid samples 20 are transmitted to the flow cell 10 with bubbles 22 of air or gas or liquid which are inert and immersible to the liquid transmitted, interspersed between successive samples. The successive fluid samples 20 pass inwardly through the bore 24 of the debubbler unit until they reach aperture 25 in its bottom surface. Due to the fact that the specific gravity of the fluid samples is heavier than the specific gravity of the air or other gas bubbles 22, the bubbles 22 continue to pass through bore 24 and exit from outlet port 26 while the fluid samples 20 would drop downwardly through aperture 25 and pass through neck portion 28 to the sight passageway or bore 30 of tubular body member 12. The air bubbles 22 and that small portion of fluid sample 20 that passes outwardly through port 26 would go to a waste disposal area.

Tubular body member 12 has a bore or sight passageway 30 that extends the entire length of the tubular member. The diameter of the bore 30 is about 1 millimeter and this would compare to the diameter of the bore 24 of the debubbler unit which is approximately one millimeter. The diameter of the bore is between 50 percent to 100 percent smaller than that of prior art flow cells. This reduced diameter results in less use of reagents and results in running the system faster and more efficiently. A reduction of up to 800 percent in the amount of reagents needed has been produced. Inserted in each of the free ends of the tubular body member 12 are light transmitting rods 32 and 33. Light transmitting rods 32 and 33 are made from quartz as is the debubbler unit 14, the tubular body member 12, and the tubular fluid outlet tower 16. Quartz is an excellent conductor of light and its transparent properties within the ultraviolet regions are especially important. As seen in FIG. 1, a light source 34 directs light through light transmitting rods 32 and through the fluid sample 20 that is passing through bore or sight passageway 30 of tubular body member 12. After the light has passed through the sample it passes through light transmitting rod 33 and is intercepted by photocell 36.

The internal end surfaces of light transmitting rod 32 and 33 form curved surfaces 38 and 39 respectively where they meet the internal surface of bore 30. This lack of 90 degree corners results from hearting to a predetermined temperature of the tubular body 12 after the light transmitting rods 32 and 33 have been inserted into the open ends of bore 30. As can be seen by looking at FIGS. 3 and 4, the curved surface is formed much in the manner of the meniscus which is formed by a liquid in a vessel adjacent the walls of the vessel. The central portion of the light transmitting rod is flat to provide optimal transmission of light.

Tubular fluid outlet tower 16 has its bottom end in communication with aperture 40 formed in the top surface of tubular body member 12. A fluid outlet port 42 is located at the top of tower 16 and the specimen sample would be passed outwardly therefrom and carried by tubular conduit to a waste station.

Referring to FIGS. 1 and 2, it will be seen that there is an opaque barrier 44 formed in the wall of tubular body member 12. Its purpose is to prevent stray light from streaming into the tubular body member from its ends which would result in inaccuracies in the readings on the photocell. Additionally an opaque coating 46 covers the entire outer surface of the flow cell 10. This is to prevent extraneous light from also entering into the walls of the tubular body member 12.

What is claimed is:

1. A flow cell for location intermediate a light source and a photosensitive device for light measurement of a fluid therein in a light path, comprising:

a body member having an open-ended bore therethrough constituting a sight passageway to lie along a portion of the length of the light path of a colorimeter;

fluid inlet means transversely connected to said open-ended bore intermediate its ends;

fluid outlet means transversely connected to said open-ended bore intermediate its ends;

said fluid inlet means and said fluid outlet means being longitudinal spaced a predetermined distance along the axis of the open-ended bore of said body member;

a pair of fluid seals in the respective open ends of said bores and closing them, each of said seals being constituted by a light transmitting rod;

said fluid inlet means and said fluid outlet means opening into said bore adjacent the respective internal ends of said light transmitting rods to define the path for fluid flowing through said sight passageway;

the internal end surface of said light transmitting rods have a central portion that is flat and substantially perpendicular to the axis of the bore of said tubular member to provide optimal transmission of light and a curved surface adjacent their perimeter that blends with the interior surface of said bore where said respective surfaces meet much in the manner of the meniscus curved surface that is formed by a liquid in a vessel due to surface tension of the liquid with the side walls of the vessel, the internal ends of said light transmitting rods being fused to the interior walls of said bore; and debubbler means comprising a tubular portion having a first aperture in its bottom surface, a tubular neck having its top end connected to said first aperture and its bottom end connected to said fluid inlet means.

2. A flow cell as recited in claim 1 wherein said body member and said light transmitting rods are made of the same material.

3. A flow cell as recited in claim 1 wherein said body member and said light transmitting rods are both made of quartz.

4. A flow cell as recited in claim 4 wherein said debubbler means is formed integrally with said body member.

5. A flow cell as recited in claim 1 wherein said body member is covered by an opaque coating.

6. A flow cell as recited in claim 1 wherein said body member has a transversely oriented opaque barrier within its cross-section that prevents light from passing longitudinally from one end to the other opposite end through the wall structure of said body member.

* * * * *